United States Patent
Roback et al.

(10) Patent No.: US 7,189,357 B2
(45) Date of Patent: *Mar. 13, 2007

(54) IMMUNOLOGICAL ASSAY SYSTEM AND METHOD

(75) Inventors: John D. Roback, Decatur, GA (US); Christopher D. Hillyer, Dunwoody, GA (US)

(73) Assignee: Emory University, Atlanta, GA (US)

( * ) Notice: Subject to any disclaimer, the term of this patent is extended or adjusted under 35 U.S.C. 154(b) by 447 days.

This patent is subject to a terminal disclaimer.

(21) Appl. No.: 09/773,826

(22) Filed: Jan. 31, 2001

(65) Prior Publication Data

US 2001/0046452 A1 Nov. 29, 2001

Related U.S. Application Data

(60) Provisional application No. 60/179,248, filed on Jan. 31, 2000.

(51) Int. Cl.
*G01N 35/00* (2006.01)

(52) U.S. Cl. .................. 422/68.1; 422/63; 422/73

(58) Field of Classification Search ............. 422/62, 422/68.1, 101, 100, 255, 63, 73
See application file for complete search history.

(56) References Cited

U.S. PATENT DOCUMENTS

| | | | | |
|---|---|---|---|---|
| 5,156,811 A | 10/1992 | White | ........................ | 422/100 |
| 5,273,718 A | 12/1993 | Skold et al. | ................ | 422/101 |
| 5,308,990 A * | 5/1994 | Takahashi et al. | ....... | 250/459.1 |
| 5,364,595 A | 11/1994 | Smith | ........................ | 422/100 |
| 5,496,523 A | 3/1996 | Gazit et al. | ................. | 422/100 |
| 5,556,598 A | 9/1996 | Raybuck et al. | .......... | 422/10 D |
| 5,603,899 A * | 2/1997 | Franciskovich et al. | .... | 422/100 |
| 5,620,898 A * | 4/1997 | Yaremko et al. | .............. | 436/45 |
| 5,762,878 A | 6/1998 | Clark et al. | ................. | 422/102 |
| 5,776,711 A | 7/1998 | Vyas et al. | .................. | 435/7.25 |
| 5,968,731 A * | 10/1999 | Layne et al. | .................... | 435/5 |
| 6,008,040 A * | 12/1999 | Datar | ......................... | 435/325 |
| 6,182,834 B1 * | 2/2001 | Kim et al. | .................. | 210/506 |

FOREIGN PATENT DOCUMENTS

| | | |
|---|---|---|
| DE | 3805808 | 9/1989 |
| DE | 4124778 | 1/1993 |
| DE | 19746455 | 5/1999 |
| FR | 2702050 | 9/1994 |

* cited by examiner

*Primary Examiner*—Jill Warden
(74) *Attorney, Agent, or Firm*—Thomas, Kayden, Horstemeyer & Risley

(57) ABSTRACT

An immunological or immunohematological assay system is disclosed that includes a filter vessel capable of containing an assay sample, an incubator, a sample separation system, an image acquisition system, and a robotic pipettor. The immunological assay system may also include a washer. Also disclosed is an immunological assay method that includes the steps of placing a immunological assay sample in a filter vessel, which includes a filter, adding testing reagents to the filter vessel, incubating the sample and reagent mixture in the filter vessel, separating the sample and reagent mixture in the filter vessel into components above and below the filter, and analyzing the filter vessel to determine the presence of interactions between the sample and reagents.

12 Claims, 3 Drawing Sheets

IMMUNOLOGICAL ASSAY SYSTEM AND METHOD

CROSS-REFERENCE TO RELATED APPLICATIONS

This application claims priority to copending U.S. provisional patent application entitled "Method for Diagnostic Laboratory Testing using DFS Columns" filed on Jan. 31, 2000 and accorded Ser. No. 60/179,248, which is entirely incorporated herein by reference.

TECHNICAL FIELD

The present invention is generally related to an immunologic assay system and, more particularly, is related to a system and method for separating components of immunological and immunohematological samples.

BACKGROUND OF THE INVENTION

Immunologic assays are designed to detect reactions between antibodies and antigens. These assays commonly employ cells, such as red blood cells (RBCs) or beads as antigen "carriers." In the appropriate assay configuration, antibodies can cross-link the antigen carriers, generating a large three-dimensional antigen-antibody aggregate from what were initially individual antigen carriers and antibodies. In other configurations, antibodies bind to the antigen carriers without cross-linking them.

Immunohematology testing in the blood bank setting uses RBCs and antibodies to determine compatibility between transfusion donor and recipient prior to transfusion. For example, the donor and recipient are incompatible if antibodies from the recipient cross-link (agglutinate) RBCs from the donor, resulting in the formation of large RBC aggregates. Current commercially available testing reagents are designed to distinguish these aggregates from individual, non-agglutinated RBCs. For example, in standard "tube testing," RBCs are mixed with antibodies, centrifuged at approximately 1000×g for a brief period, approximately 30 seconds, to enhance the formation of antigen-antibody complexes, and then gently resuspended by hand in order to be able to distinguish agglutinated from non-agglutinated RBCs. Tube testing is labor-intensive, not amenable to automation, and the results are difficult to standardize from lab to lab since they depend on the skill of the individual operator.

An alternative approach used to identify agglutinated RBCs is spin column technology, which is based on standard chromatographic principles. With this methodology, tubes filled with a homogeneous matrix material, e.g., beads, gel, or polyacrylamide, are used to separate aggregated from individual RBCs. The matrix material is designed with holes or pores of a specified size such that under carefully controlled centrifugal forces large ("4+") aggregates barely enter the matrix. However, successively smaller aggregates ("3+" through "1+") do enter the matrix to increasing degrees, and non-agglutinated RBCs not only enter the matrix, but sediment completely to the bottom of the tube. In order for a single homogeneous chromatographic matrix to effectively separate individual RBCs from RBC aggregates of various sizes, a relatively long centrifugation run, approximately 10 minutes, must be carried out under carefully controlled low-speed centrifugation conditions of 80×g. Deviations from optimal centrifugation conditions, e.g., higher centrifugation speeds in an attempt to shorten the assay run, lead to poor separation of RBCs, compromising the assay ability to determine compatibility between blood donor and recipient. This methodology is to some extent amenable to automation, and less dependent on operator skill.

Spin column technology is significantly more expensive than tube testing, due to costs of producing the columns. The matrix material is in solution, and carefully controlled packaging, shipping, and storage conditions are typically necessary. In addition, testing is slower than with tube testing because of the prolonged centrifugation step, approximately 10 minutes, versus approximately 30 seconds with tube testing. Interpretation of assay results also requires operator training, since the readout is on an "analog" scale, i.e., the distance of RBC migration through the matrix must typically be estimated.

Thus, a heretofore unaddressed need exists in the industry to address the aforementioned deficiencies and inadequacies.

SUMMARY OF THE INVENTION

The present invention provides a system and method for immunological and immunohematological assaying. Briefly described, the assay system includes a filter vessel capable of containing an assay sample, an incubator into which the filter vessel may be placed, a sample separation system in close proximity to the incubator, an image acquisition system in close proximity to the sample separation system, and a robotic pipettor including a robotic arm within reaching distance of the filter vessel, the incubator, the sample separation system and the image acquisition system. The filter vessel includes a filter that may be made of an inert material that includes a plurality of pores.

The present invention can also be viewed as providing a method for immunological and immunohematological assaying. The immunological method identifies interactions between a sample and a testing reagent where one contains an antigen carrier (RBC or bead) and the other contains an antibody. In this regard, the method can be broadly summarized by the following steps: placing an immunological assay sample into a filter vessel including a filter, adding a testing reagent to the filter vessel, incubating the sample and reagent mixture in the filter vessel, separating the sample and reagent mixture in the filter vessel into components above and below the filter, and analyzing the filter vessel to determine the presence of interactions between the sample and reagent.

In an alternative embodiment, if the step of analyzing the filter vessel produces unclear results, the method may also include the steps of placing the sample in the filter vessel in a washer, separating the antigen carrier from liquid components of the sample by capturing the antigen carrier above the filter in the filter vessel, washing the antigen carrier in the filter vessel under vacuum pressure or centrifugation with a physiological salt solution to remove excess antibody not bound to the antigen carrier, adding antibody reagents to the washed antigen carrier in the filter vessel, incubating the mixture in the filter vessel, separating the antigen carrier from liquid components of the mixture by capturing the antigen carrier above the filter in the filter vessel, and again analyzing the filter vessel to determine the presence of interactions between the sample and the reagent.

Other methods, features, and advantages of the present invention will be or become apparent to one with skill in the art upon examination of the following drawings and detailed description. It is intended that all such additional methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

In general, the present invention pertains to a system and method for separating and analyzing components of immunological and immunohematological samples. In this regard, an immunological assay system overcomes the drawbacks of current tube testing and spin column technology, while simultaneously rendering the technology of immunological assay more amenable to automation. In a preferred embodiment, the immunological assay system is an instrument that includes a filter vessel system including one or more filters that have discrete molecular weight and size cutoffs due to the presence of a plurality of holes or pores of specified sizes in the filter. An immunological sample is mixed with a reagent and placed above the filter(s). After vacuum or centrifugation or some other method of inducing the sample through the filter is applied, the components of the sample are separated from one another according to their size by the various filters.

The immunological system of the present invention can be used to measure interactions between antibodies and cells, or in some cases between antibodies and synthetic beads that can be modified and/or configured to act as antigen carriers. The immunological system can be used in at least two different ways. In one method, "cellular components" of patient samples, e.g., red blood cells (RBCs), white blood cells (WBCs), or platelets, are mixed with "reagent antibodies." The components of the mixture are separated, and then analyzed to determine the presence of interaction between the cellular components and the reagent antibodies. In another method, the immunological system may be used in an assay method that mixes patient antibody-containing samples, e.g., plasma or serum samples, with antigen carriers that may be synthetic beads or reagent cells, e.g., RBCs, WBCs, or platelets. This mixture is then separated, and the components are analyzed to determine the presence of interactions between the antibody samples and the reagent cells or synthetic beads.

Figure 1:
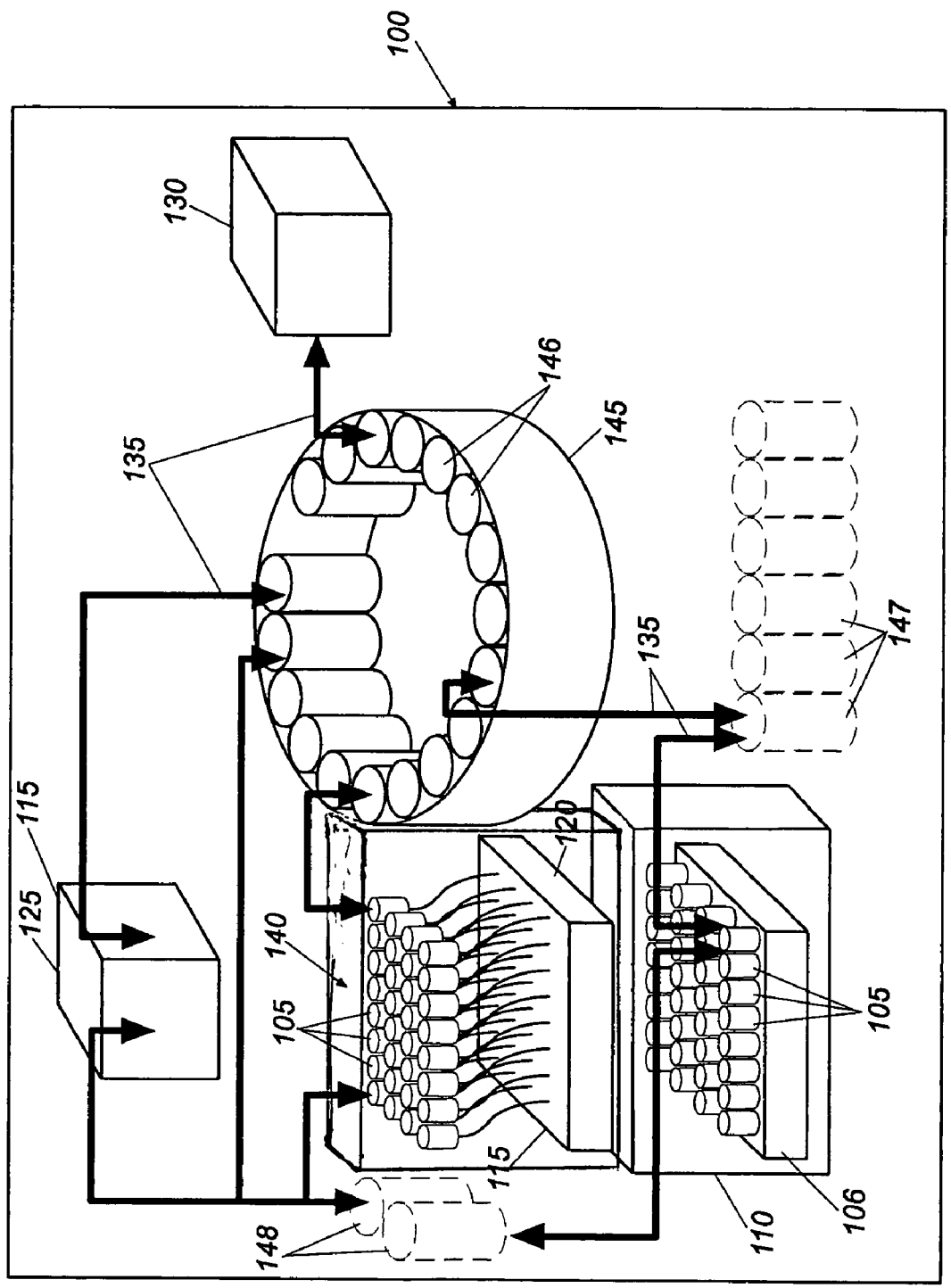
FIG. 1 is a diagram illustrating an immunological system of the present invention.

FIG. 1 depicts the immunological system 100 of the present invention. The immunological system 100 is an instrument that includes a filter vessel 105 capable of containing an assay sample, an optional incubator 110 into which the filter vessel may be placed, a sample separation system 115 disposed in close proximity to the incubator 110 or disposed therein, an optional image acquisition system 130 in close proximity to the sample separation system 115, and an optional robotic pipettor 135 that includes a robotic arm within reaching distance to the filter vessel 105, the incubator 110, the sample separation system 115 and/or the image acquisition system 130. The immunological system 100 may also include an optional washer 140 disposed therein, an optional turntable system 145 which has disposed therein sample holders 146 for holding the assay sample. Further included in the immunological system 100 may optionally be tubes with the assay sample 147 and/or tubes with reagent 148.

The optional incubator 110 disposed within the immunological system 100 is of a shape and size that allows a filter vessel 105 to be disposed therein. While many sizes and shapes of an incubator may be used, in a preferred embodiment, the incubator 110 is of a shape and size so as to allow a plurality of filter vessels 105 or a plate of filter vessels 106 to be disposed therein. The incubator 110 may further include an optional heating element capable of heating the filter vessels when they are disposed in the incubator 110.

The sample separation system 115 is also of a shape and size so as to allow a filter vessel 105 to be disposed therein. While many sizes and shapes of a sample separation system may be used, in the preferred embodiment, a plurality of filter vessels 105 and/or a plate of filter vessels 106 may be disposed therein. The sample separation system 115 may be, for example, but is not limited to, a vacuum 120, a centrifuge 125, and/or an applied electric field. The sample separation system 115 is of a type that when the filter vessel 105 is placed within the sample separation system 115, an assay sample 147 disposed within the filter vessel 105 is drawn through a filter 150, thereby separating out the assay sample into various components based on size.

The optional image acquisition system 130 may be, for example, but is not limited to, a camera, a flow cytometer, a special lens such as a microscope, or even a human eye. Usually, an assay sample is analyzed by the image acquisition system 130 after it has been removed from the sample separation system 115. The image acquisition system 130 allows analysis of the filter vessel 105 in order to determine the presence or absence of material above the filter 150 disposed within the filter vessel 105. The image acquisition system 130, particularly when it takes the form of a flow cytometer, may also be used to determine the size of the material above the filter 150, for example whether the material is in the form of individual antigen carriers or aggregates of antigen carriers, as well as to determine whether antibodies are bound to the antigen carriers that are present above the filter.

The optional robotic pipettor 135 used within the system is of the type commonly known and used by those skilled in the art. For example, but not limited to, the robotic pipettor system that is manufactured by and commercially available from Tomtec, Inc. (Hamden, Conn., U.S.A.) or CRS Robotics Corporation (Burlington, Ontario, Canada) may be used in accordance with one embodiment of the present invention.

The optional washer 140 is disposed within reaching distance of a robotic arm of the robotic pipettor 135 from the image acquisition system 130. If analysis of the material above the filter 150 in the filter vessel 105 by the image acquisition system 130 produces unclear results, the assay sample may be as disposed within the filter vessel 105 may be placed within the washer 140. The washer 140 is of a size and shape so as to allow the filter vessel 105, a plurality of filter vessels 105, and/or a plate of filter vessels 106 to be disposed therein. The washer 140 is designed so as to wash all reagents from the antigen carriers present in the assay mixture, and through the filter 150 of the filter vessel 105. While there may be many configurations of the washer 140, in the preferred embodiment, the washer 140 is the same system as the vacuum 120.

Figure 2:
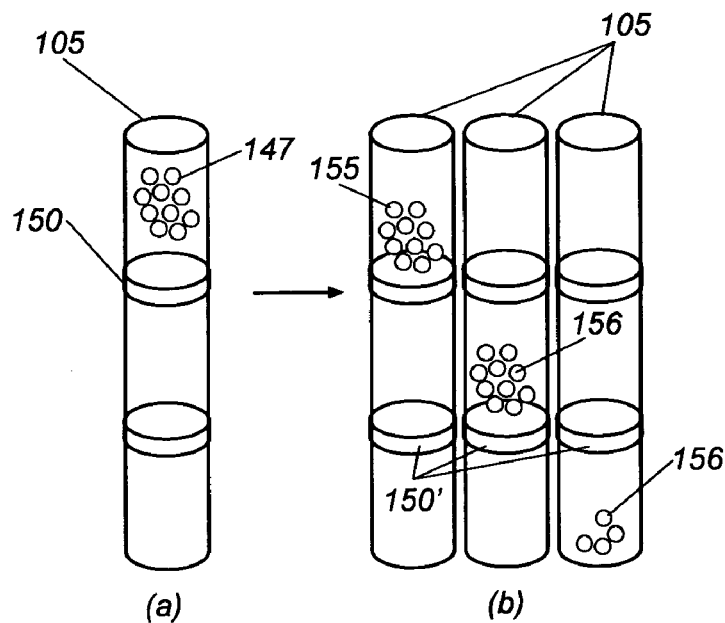
FIG. 2 is a diagram illustrating a filter vessel system, one example of the type of filter vessel that serves as a component of the immunological system of FIG. 1.

FIG. 2 depicts the filter vessel 105 component of the immunological system 100 of FIG. 1. "Filter vessel" 105 means a vessel capable of containing an assay sample and including one or more filters disposed therein. FIG. 2 represents the filter vessel 105 (a) before being placed in the sample separation system 115, and (b) after removal from the sample separation system 115. As seen in FIG. 2, disposed within the filter vessel 105 is/are one or more filters 150. The filter 150 comprises an inert material that includes a plurality of pores. The pore size of the filter 150 may be varied, according to the various embodiments of the invention. For example, pores of the filter 150 may be of a size ranging from approximately 0.01 microns to approximately 50 microns. The size of the pores of the filter 150 will depend on the application of the filter vessel 105.

If it is desired that the filter 150 be used to retain, for example, RBC aggregates, while allowing individual red blood cells to pass through the pores of the filter 150, in one embodiment of this application, the range of pore sizes is between approximately 3 microns to approximately 40 microns. While other pore sizes may be used, in the preferred embodiment, the pore size ranges from approximately 3 microns to approximately 5 microns. If, however, the filter vessel 105 is used to filter fluid away from the antigen carriers (RBCs, WBCs, platelets, or synthetic beads) where the filter 150 is used to retain the antigen carriers, but allow fluid containing antibodies to pass therethrough, the range of pore sizes in the preferred embodiment is approximately 0.1 to approximately 3 microns. The optimal pore size for this methodology is 0.2 microns.

The thickness of the filter 150 may also vary in the different embodiments of the filter vessel 105, depending upon the application of the filter 150. For example, the thickness of the filter 150 may range from approximately 3 microns to approximately 5 mm. In the preferred embodiment the filter 150 is between approximately 3 microns to approximately 100 microns. Optimally, the thickness of the filter 150 is between approximately 10 microns and approximately 75 microns.

The material used for the filter 150 may be any material in the various embodiments of the filter vessel 105, preferably an inert material, that includes a plurality of pores. The material of the filter 150 may be varied, depending on the application of the filter 150. If the function of the filter 150 is to retain RBC aggregates, while allowing individual RBCs to pass therethrough, then the filter material may be, for example, but not limited to, a polyester mesh, a nylon mesh, or a polycarbonate track-etched membrane. A filter 150 having material of this type is manufactured by and commercially available from Sefar, Inc. in Kansas City, Mo., U.S.A. If the application of the filter 150 is to retain all RBCs, but allowing other fluids containing antibodies to pass therethrough, in the preferred embodiment the filter material used is a 0.2 micron polyvinylidene difluoride filter membrane manufactured by and commercially available from Corning Life Sciences, Inc. in Acton, Mass., U.S.A. Alternatively, a supported cellulose acetate membrane, for example, Acetate Plus™ membrane manufactured by and commercially available from Osmonics, Inc. (Minneapolis, Minn., U.S.A.), may also be used for this application.

As can be seen in FIG. 2, the filter vessel 105 may contain a plurality of filters 150. If a plurality of filters 150 are used, the filters 150' disposed lower or below the first filter 150, are usually, in the preferred embodiment, of a smaller pore size, thereby breaking out an assay sample into its various components by size. As can be seen in FIG. 2, an assay sample 147 (not necessarily part of the invention) is placed within the filter vessel 105 above the first filter 150. In (b), after undergoing sample separation, the largest-sized aggregates of antigen carriers 155 of the sample 147 remain above the first filter 150. Non-agglutinated or smaller aggregates 156 of the sample 147 remain above or pass through the second filter 150'.

Figure 3:
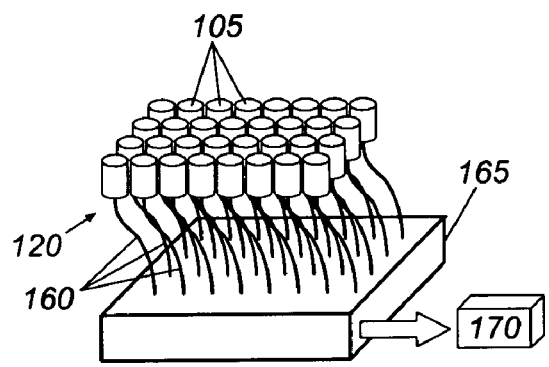
FIG. 3 is a diagram illustrating a vacuum, one example of a sample separation system component of the immunological system of FIG. 1.

FIG. 3 depicts the vacuum system 120, which is one type of sample separation system 115 component of the immunological system 100. The vacuum 120 is shown in FIG. 3 with a plurality of filter vessels 105 or a plate of filter vessels 106 disposed therein. It should be understood that included within the scope of the invention is a vacuum with one or more filter vessels included therein. Connected to the individual filter vessels 105 is vacuum tubing 160, which passes through a vacuum controller 165, which is connected to a vacuum pump 170.

The preferred configuration of the vacuum 120 as shown in FIG. 3 uses a 96-filter vessel plate format. While other configurations are possible in other embodiments, in the preferred embodiment the vacuum system vacuum 120 is one that independently contacts each of the filter vessels 105 and applies pressure to each filter 105 independently of the other filter vessels 105. In this embodiment, each filter vessel 105 of the filter vessel plate 106 (FIG. 1) is contacted underneath by an individual gasket, which is in turn is attached to an individual piece of tubing 160 that connects the filter vessels 105 to the vacuum pump 170. Thus, there are 96 segments of tubing from the pump 170 to the plate of filter vessels 106, and each segment of tubing 160 could independently have vacuum pressure switched on or off. However, it should be understood that the vacuum 120 may also apply the vacuum to a subset of filter vessels 105 at any one time, or could also apply vacuum to the entire plurality of filter vessels 105 or filter vessel plate 106 simultaneously.

The pressure that may be applied by the vacuum system may range from approximately −0.1 to approximately −100 inches mercury (in. Hg). In the preferred embodiment, the range of pressure is between approximately −0.1 to approximately −10 in. Hg. Optimally, the pressure maintained by the vacuum 120 is approximately −0.1 to approximately −3 in. Hg.

Figure 4:
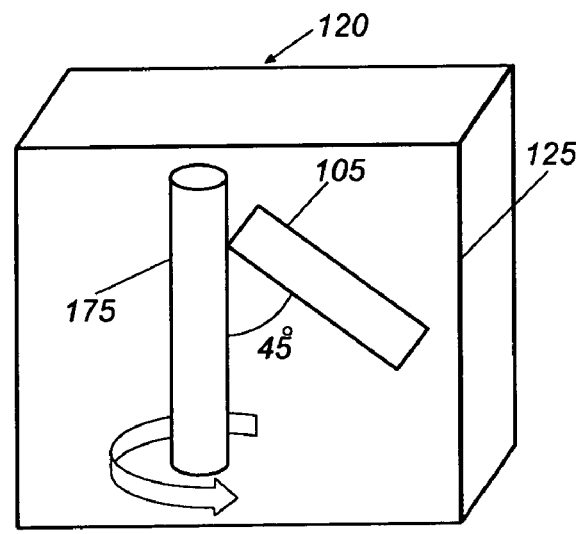
FIG. 4 is a diagram illustrating a centrifuge, another example of a sample separation system component of the immunological system of FIG. 1.

FIG. 4 depicts the centrifuge 125, which is another type of the sample separation system 115, a component of the immunological system 100. It should be understood that any type of centrifuge system known and used by those skilled in the art may be used as the centrifuge 125. For example, a typical centrifuge manufactured by and commercially available from Beckman Coulter, Inc (Fullerton, Calif., U.S.A.) may be used in accordance with one embodiment of the present invention so long as the centrifuge is modified to hold the filter vessels 105. The centrifuge 125 shown in FIG. 4 shows the angle of centrifugation used in the preferred embodiment. While many angles could work, in a preferred embodiment the filter vessel 105 is placed at a 45° angle to the axis of rotation 175.

Figure 5:
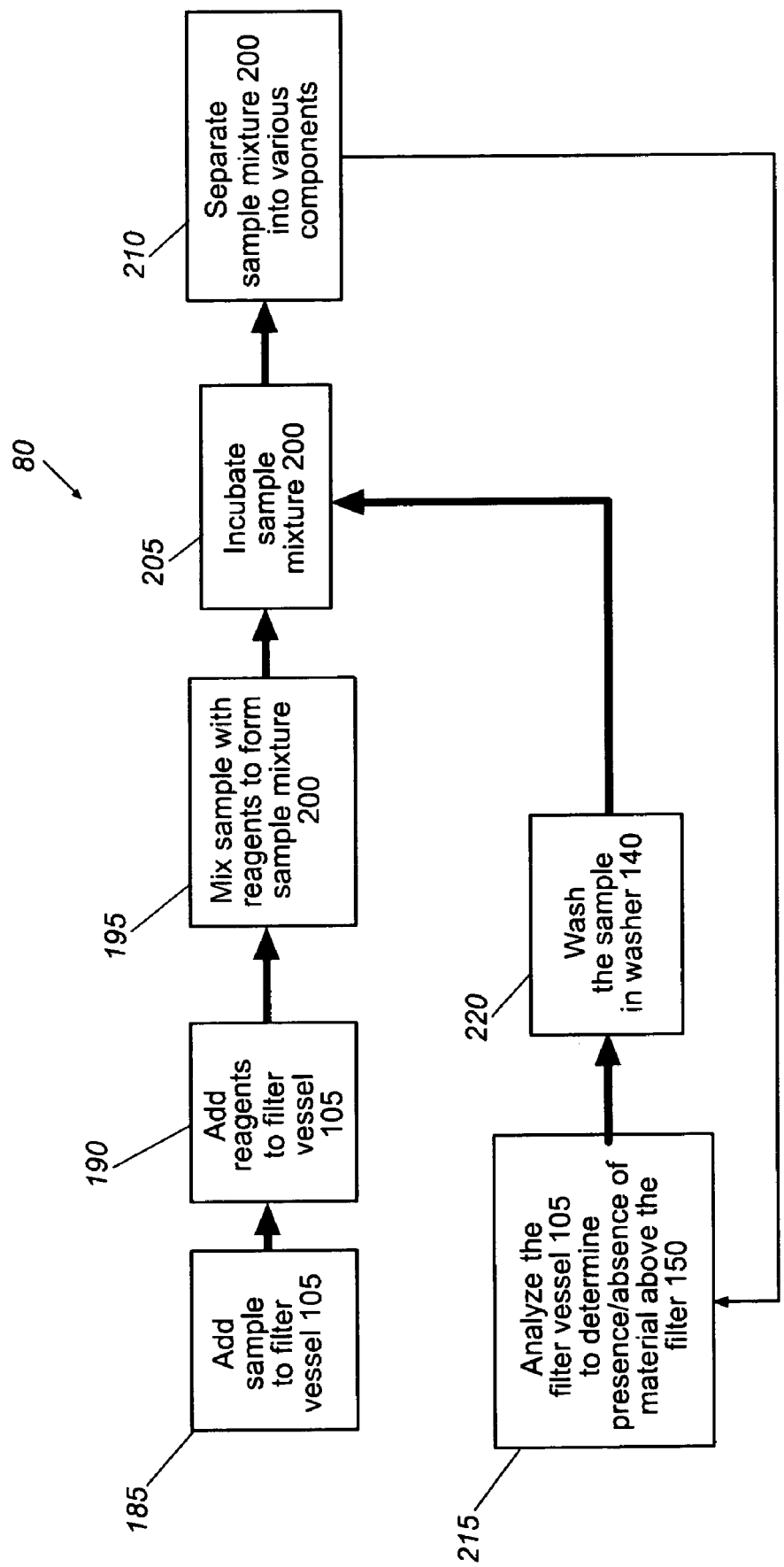
FIG. 5 is a flowchart of an immunological assay method of the present invention, which uses the immunological system of FIG. 1.

In one embodiment of the immunological system 100 of the present invention, the orientation of the filter vessel 105, the sample, and the filter 150 is such that the sample separation system 115 can cause the sample to contact the filter 150 and allow components of the sample that are smaller than the nominal pore size of the filter 150 to pass through the filter 150 into a capture reservoir below the filter 150, or the next filter 150', and thus be separated from the components of the sample that are too large to fit through the filter pores and that remain in the filter vessel 105 above the filter 150, and possibly filter 150'. Also included within the present invention is an immunological assay method. The immunological assay method 180 is depicted in the flowchart of FIG. 5. The immunological assay method 180 includes the optional step of, as can be seen block 185, placing an immunologic assay sample in the filter vessel 105. In another embodiment of the present invention, the immunological assay sample may also be placed in a standard test tube or microcentrifuge tube. Other vessels may be used for holding the assay sample in other embodiments of the method 180. Block 190 shows the next optional step of adding assay reagents to the filter vessel 105. The next step, shown in block 195, is mixing the sample with the reagent to form a sample mixture 200. Block 205 shows the optional step of incubating the sample mixture 200. In the incubation step of block 205, the sample mixture 200 may be incubated at a temperature ranging from approximately 4° C. to approximately 37° C. In a preferred embodiment, the sample mixture 200 is incubated at a temperature range between approximately room temperature (20–25° C.) and approximately 37° C. The incubation time of the sample mixture 200 can range from no incubation to approximately 30 minutes. In a preferred embodiment, the incubation time is from approximately 2 to approximately 5 minutes.

After the optional incubation step, the next optional step as depicted in block 210 is to separate the sample mixture 200 into its various components. This step is usually accomplished by placing the sample mixture 200 in the sample separation system 115. If the sample separation system 115 used in the separating step of block 210 is the centrifuge 125, the centrifuge speed is usually between approximately 10 to 10,000×g, although other speeds may be used. In the preferred embodiment, the speed of the centrifuge is between approximately 1000 to approximately 5000×g. Optimally, the speed of the centrifuge is 3000×g. The centrifuge time may range from approximately 5 seconds to approximately 5 minutes. Although other times may be used, in the preferred embodiment, the centrifuge time is between approximately 10 to approximately 30 seconds. Optimally, the centrifuge time is between approximately 15 to approximately 20 seconds.

As shown in block 215, after the optional separation step 210, the filter vessel 105 may optionally be analyzed to determine the presence or absence of interactions between the assay sample and reagent that remain above the filter 150. The sample is analyzed by placing the filter vessel 105 in the image acquisition system 130. If interactions between assay sample and reagent are detected in the material above the filter 150 by the acquisition system 130 in the analyzing step of block 215, the immunological assay method 180 is completed. Material will be detected above the filter if there have been interactions, for example, between cellular components in the assay sample and antibody reagents. The interaction will evidence itself in the form of agglutination, or clumping together, of the cellular components by the antibodies. This agglutination may be detected by the image acquisition system 130. Likewise, the absence of evidence of agglutination indicates that there were no interactions between the cellular components and the antibody reagents. Similarly, the assay method may be used to detect interactions between antibody components in the assay sample and cellular reagents by detecting presence or absence of agglutination of cellular reagents by the antibody components by the image acquisition system 130.

If the results of the analyzing step of block 215 are not clear, and no interactions are detected in the material above the filter 150 of the filter vessel 105, the immunological assay method 180 may optionally continue to the step 220 of washing the sample mixture 200 in the washer 140. As noted previously, in the preferred embodiment the washer 140 is also the vacuum 120. While vacuum may be applied for varying lengths of time according to various embodiments, in a preferred embodiment, a vacuum is applied until all fluid has been vacuumed through the filter 150 of the filter vessel system 105. The length of time the vacuum is applied is dependent on the vacuum pressure, but is often approximately 5 seconds to approximately 2 minutes, or until such time the liquid component of the sample mixture 200 has been largely or completely drawn through the filter 150.

In the optional washing step of block 220, the sample mixture 200 may be washed with a physiological salt solution. The salt solution may be for example, but not limited to, saline, e.g., 0.9% sodium chloride (NaCl) solution, a phosphate-buffered saline, or any physiological salt solution that preserves the viability of cellular components during the assay method. The washing step may comprise the steps of providing the physiological salt solution, adding approximately 10 microliters to approximately 5 milliliters of the physiological salt solution to the sample mixture 200, separating the antigen carriers, either cellular components or synthetic beads, that remain above the filter 150 from the liquid components that pass through and remain below the filter 150, and repeating these adding and separating steps from one to approximately ten times, until the sample mixture 200 is washed sufficiently for the application.

After the optional washing step of block 220, the immunological assay method 180 begins again at the optional step 190 where assay reagents are added the washed antigen carriers that remain above the filter 150 in the filter vessel 105. Following the optional mixing step 195 the resulting sample mixture 200 proceeds to the optional incubation step of block 205, wherein the sample mixture 200 is again placed in the incubator 110. Upon incubation, the sample mixture 200 is optionally placed in the sample separation system 130 as shown in block 210, and then optionally analyzed again, as shown in block 215.

In the embodiment of the present invention in which the assay sample is first placed in a standard test tube or microcentrifuge tube, the samples are assayed first with the image acquisition system 130. Then, provided the testing results of the image acquisition system 130 are unclear, the sample mixture 200 is then placed in the filter vessel 105, where it proceeds to the washing step of block 220, followed by the addition of testing reagents in block 190, the mixing of sample and reagents in block 195, the incubation step of block 205, the sample separation step of block 210, and the analysis step of block 215.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Now, therefore, the following is claimed:

1. An immunological assay system, comprising:
   a filter vessel capable of containing an assay sample of red blood cells, white blood cells, or platelets, wherein the filter vessel comprises a filter material chosen from at least one of the following: polyester mesh, nylon mesh, polycarbonate track-etched membrane, cellulose acetate membrane, and polyvinylidene difluoride filter membrane, the filter material including a plurality of pores with a pore size from about 3 microns to about 5 microns;
   an incubator in which the filter vessel may be placed, wherein the incubator houses the filter vessel while the assay sample and one or more reagent antibodies react;
   a sample separation system in close proximity to the incubator, wherein the sample separation system is designed to separate the mixture of the assay sample and the reagent antibodies into various components;
   an image acquisition system in close proximity to the sample separation system, wherein the image acquisition system consists of a flow cytometer, the flow cytometer being designed to detect the presence of interactions between reagent antibodies and the assay sample cells, wherein said interactions are evidenced by at least one of agglutinations and antigen-antibody interactions; and
   a robotic pipettor including a robotic arm within reaching distance of the filter vessel, the incubator, the sample separation system and the image acquisition system, wherein the robotic pipettor is designed to transfer the assay sample or the reagent antibodies between the filter vessel, incubator, the sample separation system and the image acquisition system.

2. The system of claim 1, further comprising a washer, wherein the washer is designed to wash the assay sample while the sample is disposed within the filter vessel.

3. The system of claim 1, wherein the filter vessel comprises a filter including an inert material including a plurality of pores.

4. The system of claim 3, wherein the filter vessel is configured to hold the assay sample such that the assay sample comes into contact with the filter material.

5. The system of claim 3, wherein the filter material has a thickness between approximately three microns and approximately five millimeters.

6. The system of claim 1, wherein the sample separation system is a centrifuge.

7. The system of claim 1, wherein the sample separation system is a vacuum system.

8. An immunological assay system, comprising:
   a filter vessel capable of containing an assay sample comprising patient antibody samples, wherein the filter vessel comprises a filter material chosen from at least one of the following: polyester mesh, nylon mesh, polycarbonate track-etched membrane, cellulose acetate membrane, and polyvinylidene difluoride filter membrane, the filter material including a plurality of pores with a pore size from about 0.1 microns to about 3 microns;
   an incubator in which the filter vessel may be placed, wherein the incubator houses the filter vessel while the assay sample and one or more reagent cells react, wherein the reagent cells are antigen carriers and are chosen from at least one of the following: red blood cells, white blood cells, and platelets;
   a sample separation system in close proximity to the incubator, wherein the sample separation system is designed to separate the mixture of the assay sample and reagent cells into various components;
   an image acquisition system in close proximity to the sample separation system, wherein the image acquisition system consists of a camera, the camera being configured to detect the presence of interactions between the reagent cells of and the assay sample antibodies, wherein said interactions are evidenced by at least one of agglutinations and antigen-antibody interactions; and
   a robotic pipettor including a robotic arm within reaching distance of the filter vessel, the incubator, the sample separation system and the image acquisition system, wherein the robotic pipettor is designed to transfer the assay sample or the reagent cells between the filter vessel, incubator, the sample separation system and the image acquisition system.

9. An immunological assay system comprising:
   a filter means, wherein the filter means is chosen from at least one of the following: polyester mesh, nylon mesh, polycarbonate track-etched membrane, cellulose acetate membrane, and polyvinylidene difluoride filter membrane, the filter means including a plurality of pores with a pore size from about 0.1 microns to about 3 microns;
   means for incubating in the filter means antibodies and antigen carriers, wherein the antigen carriers are chosen from at least one of the following: red blood cells, white blood cells, and platelets;
   means for separating the agglutinated antigen carriers or reacted antibodies and antigen carriers from fluid containing the unreacted antibodies or antigen carriers in the filter means into components above and below; and
   a flow cytometer configured to analyze the components above or below, or both above and below the filter, wherein the flow cytometer is also configured to determine the presence of interactions between the antibodies and antigen carriers, wherein said interactions are evidenced as at least one of aggregated components and antigen-antibody interactions.

10. The system of claim 9, wherein the filter means is a filter vessel.

11. The system of claim 9, wherein the means for separating the sample and reagent mixture is a centrifuge.

12. The system of claim 9, wherein the means for separating the sample and reagent mixture is a vacuum system.

* * * * *